United States Patent [19]

Kremer

[11] 4,456,179

[45] Jun. 26, 1984

[54] MIST GENERATOR AND HOUSING THEREFOR

[75] Inventor: Ann S. Kremer, Darien, Conn.

[73] Assignee: Eastfield Corporation, Darien, Conn.

[21] Appl. No.: 350,273

[22] Filed: Feb. 19, 1982

Related U.S. Application Data

[63] Continuation of Ser. No. 206,049, Nov. 12, 1980, abandoned, which is a continuation of Ser. No. 118,527, Feb. 4, 1980, abandoned, which is a continuation of Ser. No. 900,881, Apr. 28, 1978, abandoned.

[51] Int. Cl.³ .............................................. B05B 7/30
[52] U.S. Cl. .................................................. 239/338
[58] Field of Search ............... 128/193, 194; 239/338, 239/370; 261/DIG. 65, 78 A

[56] References Cited

U.S. PATENT DOCUMENTS

| 743,866 | 11/1903 | Harris | 239/338 |
|---|---|---|---|
| 824,471 | 6/1906 | Eggers | 239/338 X |
| 1,839,193 | 1/1932 | Blanchard | 239/338 X |
| 2,329,506 | 9/1943 | Ailes | 239/338 X |
| 2,826,454 | 3/1958 | Coanda | 239/338 |
| 3,826,255 | 7/1974 | Havstad et al. | 239/338 X |
| 3,864,326 | 2/1975 | Babington | 239/338 X |
| 4,116,387 | 9/1978 | Kremer et al. | 239/338 |

FOREIGN PATENT DOCUMENTS

| 58878 | 4/1954 | France | 239/338 |
|---|---|---|---|
| 640808 | 7/1950 | United Kingdom | 239/338 |

Primary Examiner—John J. Love
Attorney, Agent, or Firm—Eugene E. Geoffrey, Jr.

[57] ABSTRACT

A mist generator which includes a frusto-conical housing having a base forming a reservoir and a narrowed outlet opening, a mist generator within said housing and extending upwardly from said base, said generator discharging said mist in the space within said housing and surrounding the generator whereby said mist emerges from the housing through the narrowed outlet opening. The housing may further include ribs on the inner surface thereof, a gas chamber for receiving compressed gas and then feeding it to the mist generator and at least one opening for feeding liquid to the reservoir while the mist is being produced.

4 Claims, 10 Drawing Figures

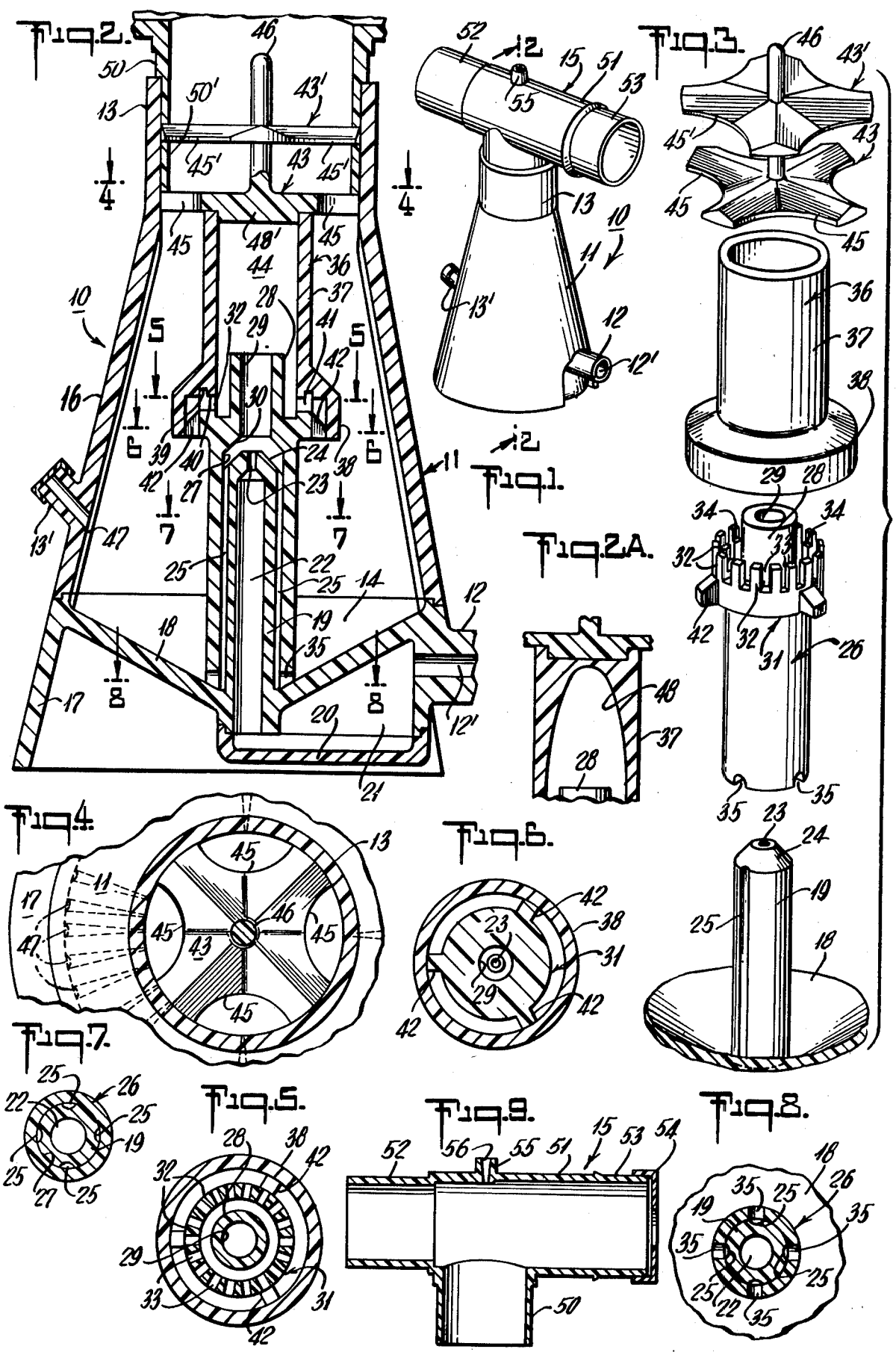

MIST GENERATOR AND HOUSING THEREFOR

This application is a continuation of application Ser. No. 206,049, filed Nov. 12, 1980 entitled "Improved Mist Generator and Housing Therefor" now abandoned, which was a continuation of application Ser. No. 118,527, filed Feb. 4, 1980 entitled "Improved Mist Generator and Housing Therefor", now abandoned, which was a continuation of application Ser. No. 900,881, filed Apr. 28, 1978, entitled "Improved Mist Generator and Housing Therefor", now abandoned.

This invention relates to mist generators and constitues an improvement of the mist generator disclosed in a copending application for patent entitled MIST GENERATOR, filed May 11, 1976, Ser. No. 685,307 now U.S. Pat. No. 4,116,387.

The aforementioned application concerns a mist generator embodying an improved nebulizer which includes means forming a circuituous path for movement and agitation of the mist and results in the production of a mist having exceeding fine particles. The generator is particularly useful for a variety of purposes including therapeutic applications such as the treatment of lung disorders, humidification, and the spraying of paints, oils, insecticides, fertilizers and other liquids.

On object of the invention resides in the provision of a novel and improved housing for a mist generator which receives the mist prior to discharge and functions to remove larger particles and produce a submicron mist of more uniform particle size.

Another object of the invention resides in the provision of an improved housing for a mist generator which includes a chamber interposed between the compressed air or gas inlet and aspirating nozzle and functions as a low pass filter to provide a smoother flow of gas to the nozzle when the gas is supplied from a suitable pump such as a reciprocating or vane pump.

The invention, when utilized for the treatment of lung disorders, further contemplates an improved mouthpiece for use with the generator including means for feeding liquid to the generator during the operation thereof.

The invention involves a novel and improved frusto-conical housing for a mist generator which receives the mist produced by the generator and functions to remove larger particles prior to discharge through an outlet at the top of the housing. The mist generator is carried by the dished bottom of the housing and has a aspirator including a nozzle extending upwardly from the bottom of the housing and through which compressed air is fed. The liquid contained in the bottom is aspirated through channels surrounding the nozzle to produce a mist which is then fed through a succession of chambers to agitate it so that the resultant turbulence effects the removal of a large proportion of the larger particles. While the mist generator produces in the large part submicron particles of less than 0.1 micron, the remaining larger particles upon being discharged into the housing, will, because of inertia, strike the wall of the tapered housing and be returned to the reservoir formed by the dished bottom. The walls of the housing may also be ridged to facilitate interception of the larger particles. Thus, the improved housing not only insures the production of a mist of more uniform particle size, but also provides a large reservoir which being dished will cause the liquid to accumulate at the center of the reservoir from which point it is aspirated to produce the mist. In this way, more efficient utilization of the liquid is obtained which is particularly important in therapeutic applications requiring patients to be given prescribed dosages.

The above and other objects and advantages of the invention will become more apparent from the following description and accompanying drawings forming part of this application.

IN THE DRAWINGS

FIG. 1 is a perspective view of a novel and improved nebulizer in accordance with the invention.

FIG. 2 is an enlarged cross sectional view of FIG. 1 taken along the line 2—2 thereof.

FIG. 2a is a fragmentary portion of FIG. 2 showing a modified embodiment of a chamber therein.

FIG. 3 is an exploded view of the nebulizing structure enclosed within the outer housing as shown in FIG. 2.

FIGS. 4, 5, 6, 7 and 8 are cross sectional views of FIG. 2 taken along the lines 4—4, 5—5, 6—6, 7—7 and 8—8 of FIG. 2 and;

FIG. 9 is a cross sectional view of the T-tube disposed on top of the nebulizer as illustrated in FIG. 1.

As previously pointed out the nebulizer in accordance with this invention comprises a novel and improved arrangement of elements which functions to produce a more uniformly fine mist by removal of the larger and undesirable particles. This is attained through the utilization of a frusto-conical housing containing the mist generator and which housing preferably includes a ribbed inner surface. The housing being substantially larger at the bottom portion facilitates the retention of a larger quantity of liquid to be nebulized and this is particularly advantageous when the nebulizer is being used for therapeutic purposes since a wider range of dosages is available. The improved housing further includes a chamber which is positioned in series with the air supply used to nebulize the liquid and this chamber functions as a low pass filter to provide a relatively steady flow of air or other gas which is usually derived from a small compressor.

Referring now to the drawings, and more specifically, to FIGS. 1 and 2, the nebulizer is generally denoted by the numeral 10 and comprises an outer frusto-conical housing 11, a compressed air inlet 12 and an outlet 13 for the nebulized liquid 14 contained within the housing 11. A T-tube 15 may be affixed to the top of the nebulizer housing 11 as illustrated in FIG. 1. This T-tube is particularly useful when the device is being employed for therapeutic purposes. It will be understood however, that the nebulizer in accordance with the invention is useful for nebulizing other liquids such as oils, paints, chemical solutions and the like when it is desired to obtain a mist having an exceedingly fine particles.

More specifically the housing 11 consists of a frusto-conical portion 16 terminating in a cylindrical outlet 13, a base portion 17, and a capped liquid inlet 13' for feeding liquid to the reservoir prior to or during the course of producing the mist. The base portion 17 includes a dished or conical bottom or reservoir 18 which carries a nozzle 19 extending upwardly from the center thereof. At least a portion of the space below the bottom 18 is closed by a cap 20 to form a closed chamber 21 to receive compressed air or gas entering through the opening 12' on the inlet 12. The nozzle 19 has a central opening 22 which communicates with the chamber 21 and terminates at its upper end in a small opening 23.

The upper end of the nozzle 19 is provided with a 45° bevil as denoted by the numeral 24. The annular configuration of the end of the nozzle has been found particularly useful in producing a fine mist. It is evident, however, that angles differing from 45° may also be utilized.

The nozzle 19, as viewed in FIGS. 3 and 8, has a plurality of channels 25 formed in the surface thereof. A sleeve like structure 26 having a central opening 27 slidably receives the nozzle 19 as will be observed more clearly in FIGS. 2, 7 and 8. The cylindrical structure 26 causes the liquid to be nebulized to be drawn upwardly through the channels 25.

The upper end 28 of the cylindrical structure 26 is of reduced diameter and has an opening 29 also of reduced diameter and which communicates with the opening 27. The opening 27 terminates above the end of the nozzle 19 in a conical convergent portion 30, preferably at a 45° angle, which communicates with the opening 29. The cylindrical sturcture further includes an annular portion 31 of enlarged diameter which has a plurality of spaced upwardly extending elements 32 forming intervening slots 33. The upper end of each of the elements 32 is of reduced section to form a shoulder 34 as will be observed more clearly in FIG. 3. The bottom end of the cylindrical structure includes a plurality of slots or grooves 35 to admit fluid to the channels or grooves 25, formed in the nozzle 19, during the aspirating process.

A second cylindrical structure 36 is arranged to cooperate with the cylindrical structure 26 as will be observed more clearly in FIGS. 2 and 3. The structure 36 has a cylindrical portion 37 terminating in a lower portion 38 of enlarged diameter and in the nature of a skirt. The inner surface of the skirt portion 38 as viewed in FIG. 2 has an annular recess 39 to receive the upper ends of the elements 32 with the shoulder 34 of the elements 32 bearing against the surface 40 as will be observed in FIG. 2. With this arrangement the spaced elements cooperate with the tubular or cylindrical structure 36 to form a plurality of openings 41. The structure 26 also includes a plurality of outwardly extending spacing or aligning members 42 which engage in the inner surface of the skirt portion 38 as shown in FIG. 2 to insure proper alignment of the two cylindrical structures 26 and 36.

The top of the cylindrical structure 36 is closed by a top cap 43 having an annular portion 48' engaging the top of the cylindrical portion 37 of the structure 36 to form a closed chamber 44. A plurality of recesses 45 are formed in the edge of the top cap to permit the flow of the mist upwardly into the T-tube 15 or be discharged into the atmosphere or other tubing that may be connected thereto. To facilitate removal of the top cap 43, a short rod like extension 46 is secured thereto which can be readily gripped by the fingers.

With the apparatus thus far described, a liquid to be nebulized is placed in the bottom of the housing 16 surrounding the nozzle 19. Air is fed through the opening 12' into the chamber 21 whereupon it is discharged upwardly through the openings 22 and 23 in the nozzle 19. This aspirates the liquid which is drawn up through the channels 25 in the side of the nozzle 19 and produces a mist which enters a first chamber directly ahead of the nozzle. The mist then passes into a second chamber formed by the opening 29 in the tubular member 28 whereupon it is discharged into chamber 44. The mist then passes downwardly and is exhausted through the openings 41 formed by the spaces 33 between the vertically disposed elements 32 and into the frusto-conical housing surrounding the nebulizing structure. The resultant mist is then discharged upwardly through the recesses or openings 45 in the top cap 43.

The particles generated by this nebulizer while in the submicron particle size nevertheless, do include particles that may range in the order of a half micron or possibly larger. While a substantial portion of these larger particles are removed by reason of the turbulence created in the production of the mist in its direction through the chambers and ports, some of the larger particles, nevertheless, remain and are discharged with the mist. Since the smaller particles being considerably lighter in weight tend to rise on entering the chamber surrounding the nozzle and the structure forming the chamber 44, the heavier particles however tend to continue in a given path or possibly rise only slightly. A substantial portion of these larger particles therefore strike the converging housing wall and are returned to the reservoir. Further improvement in the removal of large particles may be attained by the utilization of a plurality of ridges 47 formed on the inner side of the wall 16. These ridges tend to intercept more of the larger particles and either break them up into smaller particles or return the liquid back to the reservoir. The ridges are preferably of the order of 0.85 mm to 2 mm in height and may be spaced 1 to 5 mm apart. The height of the ridges will be dependent on the viscosity of the liquid being nebulized.

In order to further increase the turbulence of the mist as it enters the chamber 44, the latter may be provided with an elliptical, parabolic or hyperbolic curvature as shown at 48 in FIG. 2a.

The inclination of the wall 16 of the housing should preferably be of the order of 50° to 80° with the base of the cone in order to constrict the mist. Since the larger particles emerging through the openings 41 will tend to move outwardly a greater distance than the finer particles constriction of the mist will have the effect of intercepting the larger particles and thus, provide a more uniformly fine mist. It has been found that particle sizes as small as 0.0056 microns can be produced with this apparatus and while the particles will vary in size a relatively small portion of the particles exceed 0.1 microns.

As previously pointed out one of the uses of this invention involves the treatment of lung disorders and for that purpose the T-tube 15 is utilized. The tube has a tubular portion 50 adapted to engage the tubular portion 13 on the top of the housing 11 and a transverse portion 51. On one end of the transverse portion there is a tubular outlet 52 of slightly reduced diameter which is adapted to receive a suitable mouthpiece for use by the patient.

The opposing end portion 53 may remain open to the air or may include a cap 54 or other suitable means to restrict or control the flow of air into the T-tube. If desired a suitable hose can be attached in place of the cap 54 for feeding oxygen or mixtures of oxygen with air as may be desired. The top of the T-tube includes a small tubular portion 55 having an opening 56 therein for the purpose of attaching a tube for introducing liquid into the housing 11. By controlling the flow of liquid into the housing any prescribed quantity of liquid can be nebulized. When feeding liquid through the opening 56, collection on surfaces such as the top cap should be avoided. Accordingly, the top cap 43 is preferably formed with curved upper surfaces on the outwardly extending legs. In this way should one of the legs intercept the liquid drops they will not collect on the surface. If desired a second top cap 43' formed in the same manner as the cap 43 may be positioned above the cap 43 and spaced therefrom by a spacer 50'. In such a case the caps 43 and 43' may be offset by about 90°.

It is understood that while the nebulizer in accordance with this invention is highly advantageous for use in therapeutic applications the fine mist is equally useful for humidification of the air and spraying of all forms of liquid such as paints, oil, insecticides, fertilizers and the like. In addition while the illustrated embodiment of the invention provides a reservoir in which liquid is placed, it is, of course, possible to affix a liquid inlet to provide controlled rate of admission of liquid to the reservoir so that the device can operate continuously.

While only certain embodiments of the invention have been illustrated and described it is understood that alterations, changes and modifications may be made without departing from the true scope and spirit thereof.

What is claimed is:

1. A mist generator comprising a frusto-conical housing having a relatively large base, a small outlet opening on the top thereof, and a closed bottom wall forming a liquid reservoir, means within said housing for generating a mist, the last said means including means for producing a mist, means defining a closed chamber, the mist producing means extending into said chamber defining means for discharging said mist within said chamber, said chamber defining means having a plurality of outlets disposed rearwardly thereof for discharging said mist into the conical space defined by said housing and in a direction downwardly and outwardly from said outlets whereby certain of the larger particles of appreciable mass return directly to the reservoir while other of the larger particles move through paths of relatively large radii striking the frusto-conical housing wall for return to the reservoir while the small particles of said mist are carried upwardly with the air stream and are discharged from said housing outlet.

2. A mist generator according to claim 1 including a baffle surrounding said chamber and in spaced overlying relationship with said outlets.

3. A mist generator according to claim 1 wherein the inner surface of said frusto-conical housing is ribbed.

4. A mist generator according to claim 3 wherein said ribs extend between the base and said outlet opening.

* * * * *